United States Patent
Shingai et al.

(10) Patent No.: US 6,414,182 B1
(45) Date of Patent: Jul. 2, 2002

(54) PRODUCTION PROCESS FOR HYDROXYALKYL ESTER

(75) Inventors: Yasuhiro Shingai; Tokumasa Ishida, both of Himeji; Fumio Shibusawa, Ibo-gun; Tetsuya Kajihara, Himeji; Yukihiro Yoneda, Himeji; Hajime Matsumoto, Himeji; Masatoshi Ueoka, Himeji, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/620,546

(22) Filed: Jul. 22, 2000

(30) Foreign Application Priority Data

Aug. 16, 1999 (JP) .............................. 11-229706
Apr. 3, 2000 (JP) ....................... 2000-101408

(51) Int. Cl.⁷ .............................................. C07C 67/28
(52) U.S. Cl. ...................................... 560/209; 560/240
(58) Field of Search ................... 560/240, 209

(56) References Cited

U.S. PATENT DOCUMENTS

| 3,340,295 A | 9/1967 | Wheeler et al. |
| 3,632,854 A | 1/1972 | Randall |
| 3,804,884 A | * 4/1974 | Jeffrey et al. |
| 3,987,090 A | 10/1976 | Gruber et al. |
| 4,970,333 A | * 11/1990 | Rabon, Jr. et al. |
| 5,354,896 A | * 10/1994 | Pike et al. |

FOREIGN PATENT DOCUMENTS

| JP | 41-13019 | 7/1966 |
| JP | 43-18890 | 8/1968 |
| JP | 46-37805 | 11/1971 |
| JP | 51-133227 | 11/1976 |
| JP | 61-27945 | 2/1986 |
| JP | 64-6182 | 2/1989 |
| JP | 6-720 | 1/1994 |
| JP | 10-237021 | 9/1998 |

* cited by examiner

Primary Examiner—Paul J. Killos

(57) ABSTRACT

The present invention provide a production process for a hydroxyalkyl ester which comprises the step of carrying out a reaction between a carboxylic acid and an alkylene oxide in the presence of a catalyst, wherein the production process sufficiently enhances the conversion or selectivity in the reaction. The production process is characterized in that the reaction is carried out in a reaction liquid under conditions where a relationship $a<b$ is kept throughout the reaction wherein "a" is a molar concentration (mol %) of the carboxylic acid in the reaction liquid and wherein "b" is a molar concentration (mol %) of the alkylene oxide in the reaction liquid.

20 Claims, 3 Drawing Sheets

PRODUCTION PROCESS FOR HYDROXYALKYL ESTER

BACKGROUND OF THE INVENTION

A. Technical Field

The present invention relates to a production process for a hydroxyalkyl ester which comprises the step of carrying out a reaction between a carboxylic acid and an alkylene oxide.

B. Background Art

As to production processes for a hydroxyalkyl ester which comprises the step of carrying out a reaction between a carboxylic acid and an alkylene oxide, conventional ones have problems in respect to conversion or selectivity in the reaction, for example, in that they involve the formation of by-products such as alkylene glycol dicarboxylates and dialkylene glycol monocarboxylates. Thus, various studies are made to enhance the conversion or selectivity in the reaction.

For example, it is known that if the alkylene oxide is supplied to a reactor in a molar quantity excessive to (meth)acrylic acid, then the formation of the by-products is inhibited, with the result that the conversion or selectivity in the reaction is enhanced (e.g. JP-B-013019/1966, JP-B018890/1968). In addition, JP-B-006182/1989 discloses a process in which metaboric acid is used jointly with a chromium catalyst to enhance the selectivity in the reaction, and JP-A-133227/1976 discloses a process in which the reaction is carried out in the presence of a protonic acid having a boiling point higher than that of the aimed ester, and JP-A-027945/1986 discloses a process in which the reaction is carried out with a trivalent chromium compound used as a catalyst in a manner such that the wavelength which exhibits the maximum absorbance in the wavelength range of not less than 500 nm in a visible absorption spectrum of the reaction liquid can be more than 575 nm at the end of the reaction.

However, the enhancement of the conversion or selectivity in the reaction by these conventional processes cannot be said to be sufficient.

SUMMARY OF THE INVENTION

A. Object of the Invention

An object of the present invention is to provide a production process for a hydroxyalkyl ester which comprises the step of carrying out a reaction between a carboxylic acid and an alkylene oxide, wherein the production process can sufficiently enhance the conversion or selectivity in the reaction.

B. Disclosure of the Invention

The present inventors diligently studied to solve the above problems. As a result, they completed the present invention by finding that if not the ratio between the carboxylic acid and the alkylene oxide as charged as raw materials, but the molar concentrations of the carboxylic acid and the alkylene oxide in the actual reaction liquid were controlled so as to satisfy a certain relationship throughout the reaction, then the selectivity in the reaction would sufficiently be enhanced, and further, the conversion in the reaction would also be enhanced.

That is to say, a production process for a hydroxyalkyl ester, according to the present invention, comprises the step of carrying out a reaction between a carboxylic acid and an alkylene oxide in the presence of a catalyst, with the production process being characterized in that the reaction is carried out in a reaction liquid under conditions where a relationship a<b is kept throughout the reaction wherein "a" is a molar concentration (mol %) of the carboxylic acid in the reaction liquid and wherein "b" is a molar concentration (mol %) of the alkylene oxide in the reaction liquid.

These and other objects and the advantages of the present invention will be more fully apparent from the following detailed disclosure.

DETAILED DESCRIPTION OF THE INVENTION

Figure 1:
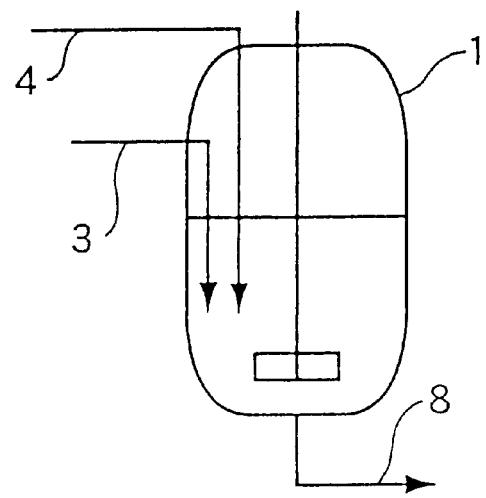
FIG. 1 is an illustration of one mode for carrying out the present invention in which a single tank reactor is used.

First, the production process for a hydroxyalkyl ester to which the characteristic production process according to the present invention is preferably applicable is roughly explained as follows.

First, an addition reaction between the carboxylic acid and the alkylene oxide is carried out in the presence of a catalyst. The conversion in this addition reaction is often less than 100%, therefore generally such as a portion of the carboxylic acid or alkylene oxide remains unreacted in the reaction at the end of the reaction. Thus, the above reaction liquid is led to the step to remove such as these unreacted residues of raw materials from the reaction liquid, and then purified by such as distillation as the subsequent final step, with the result that the aimed hydroxyalkyl ester is obtained.

Hereinafter, the step of the addition reaction between the carboxylic acid and the alkylene oxide in the presence of a catalyst (this step is a character of the present invention) is explained.

When the present invention is carried out, the amount of raw materials as charged for the above reaction between the carboxylic acid and the alkylene oxide is such that the alkylene oxide is preferably not smaller than 1 mol, more preferably in the range of 1.0~5.0 mols, still more preferably in the range of 1.0~3.0 mols, yet still more preferably in the range of 1.0~2.0 mols, per 1 mol of the carboxylic acid. In the case where the amount of the alkylene oxide as charged is smaller than 1.0 mol, there are disadvantages in that the conversion is lowered to increase the by-products. In addition, in the case where the amount of the alkylene oxide as charged is too large, particularly, larger than 5 mols, there are economical disadvantages.

Examples of the carboxylic acid usable in the present invention include acrylic acid, methacrylic acid, acetic acid, propionic acid, butyric acid, maleic acid, fumaric acid, succinic acid, benzoic acid, terephthalic acid, trimellitic acid, and pyromellitic acid, but acrylic acid and methacrylic acid (which are generically referred to as (meth)acrylic acid) are particularly preferable. In addition, the alkylene oxide, usable in the present invention, preferably has 2~6 carbon atoms, more preferably 2~4 carbon atoms. Examples thereof include ethylene oxide, propylene oxide, and butylene oxide. Among them, ethylene oxide and propylene oxide are preferable, and ethylene oxide is particularly preferable.

In the present invention, the reaction between the carboxylic acid and the alkylene oxide in the presence of a catalyst can be carried out by methods which are used conventionally for this kind of reaction.

For example, in the case where the reaction is carried out in a batch manner, the reaction is carried out by introducing the alkylene oxide into the carboxylic acid in a state where the alkylene oxide is liquid. In the case where the carboxylic acid is a solid, the carboxylic acid may be dissolved into a solvent, and then the alkylene oxide may be introduced into the resultant solution. In this batch manner, the alkylene oxide may be added all at once, or continuously or intermittently. And in the case where the alkylene oxide is added continuously or intermittently, it is permissible that, as is often the case with this kind of reaction, the reaction is continued still after the introduction of the alkylene oxide, in other words, aging is carried out, thereby completing the reaction. In addition, the carboxylic acid does not need to be charged all at once in the initial stage, but can be added after being divided into some portions.

In addition, in the case where the reaction is carried out in a continuous manner, the reaction is carried out by continuously adding the carboxylic acid and the alkylene oxide into a reactor such as tubular or tank reactor in a state where the alkylene oxide is liquid, and continuously extracting the resultant reaction liquid from the reactor. In this continuous manner, the catalyst may continuously be supplied together with raw materials and then continuously be extracted together with the resultant reaction liquid and, in the case of a reactor such as tubular reactor, a solid catalyst may be used in a state filled in the reactor, in other words, in what is called a fixed bed manner. In addition, in the case of the tank reactor, a solid catalyst may be used in a state fluidized together with the reaction liquid in the reactor, in other words, in what is called a fluidized bed manner. In the cases of these continuous reactions, a part of the reaction liquid may be circulated.

As to the addition of the raw carboxylic acid and the raw alkylene oxide into the reactor, they may be added from their separate lines, or they may be premixed together in such as piping, a line mixer, or a mixing tank and then added into the reactor. In addition, in the case where a reactor outlet liquid is circulated into a reactor inlet, or in the case where an unreacted residue of the alkylene oxide or carboxylic acid is recovered and then recycled, these liquids may be mixed with the raw carboxylic acid or the raw alkylene oxide and then added into the reactor. However, in the case where the raw carboxylic acid and the raw alkylene oxide are added from their separate feeding lines into the reaction liquid, the molar ratio in the reaction liquid is such that the carboxylic acid is excessive near an inlet into which the carboxylic acid is added, therefore it is preferable that the above raw materials are premixed together in such as piping and then added into the reactor.

The reaction temperature is usually in the range of preferably 40~130° C., more preferably 50~100° C. In the case where the reaction temperature is lower than 40° C., there are disadvantages in that the reaction rate is so slow as to be apart from a practical use level. On the other hand, in the case where the reaction temperature is higher than 130° C., there are disadvantages in that a large amount of by-products are formed, or in that, when the raw carboxylic acid has an unsaturated double bond, such as polymerization of this carboxylic acid or product hydroxyalkyl ester occurs.

In addition, the reaction may be carried out in a solvent for the purpose of, for example, mildly running the reaction. As to the solvent, conventional ones such as toluene, xylene, heptane, and octane are usable. The pressure in the reaction system during the reaction depends on the kinds or mixing ratios of the raw materials, but is generally higher than atmospheric pressure.

In addition, when the reaction is carried out, conventional polymerization inhibitors are usable. Examples thereof include: phenol compounds such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, and hydroquinone monomethyl ether; paraphenylenediamines such as N-isopropyl-N'-phenyl-para-phenylenediamine, N-(1,3-dimethylbutyl)-N'-phenyl-para-phenylenediamine, N-(1-methylheptyl)-N'-phenyl-para-phenylenediamine, N,N'-diphenyl-para-phenylenediamine, and N,N'-di-2-naphthyl-para-phenylenediamine; amine compounds such as thiodiphenylamine and phenothiazine; copper dialkyldithiocarbamates such as copper dibutyldithiocarbamate, copper diethyldithiocarbamate, and copper dimethyldithiocarbamate; nitroso compounds such as nitrosodiphenylamine, isoamyl nitrite, N-nitrosocyclohexylhydroxylamine, N-nitroso-N-phenyl-N-hydroxylamine, and their salts; and N-oxyl compounds such as 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5)decane-6-oxyl, 2,2,6,6-tetramethyl-4-acetoxypiperidine-1-oxyl, and 2,2,6,6-tetramethyl-4-benzoyloxypiperidine-1-oxyl. The amount of the polymerization inhibitor as added is in the range of preferably 0.0001~1 weight %, more preferably 0.001~0.5 weight %, of the carboxylic acid.

The production process according to the present invention is characterized in that the reaction is carried out in a reaction liquid under conditions where a relationship a<b is kept throughout the reaction wherein "a" is a molar concentration (mol %) of the carboxylic acid in the above reaction liquid and wherein "b" is a molar concentration (mol %) of the alkylene oxide in the above reaction liquid. If the reaction is controlled in this way that the relationship a<b is kept throughout the reaction, then the selectivity in the reaction is sufficiently enhanced, and further, the conversion in the reaction is also enhanced. The method for controlling the reaction so as to keep the relationship a<b throughout the reaction is not especially limited, but examples thereof include the below-mentioned method in which the raw carboxylic acid is divided and then added to keep the molar concentrations in the reaction liquid so as to satisfy the relationship a<b. In addition, in the case where water is present in the reaction liquid, the alkylene oxide is consumed by forming into an alkylene glycol, therefore the alkylene oxide is more consumed in the reaction liquid than the carboxylic acid is, with the result that the molar concentrations in the reaction liquid cannot be kept so as to satisfy the relationship a<b. Thus, a method for keeping the molar concentrations in the reaction liquid so as to satisfy the relationship a<b is exemplified, in which the formation of the alkylene glycol is decreased to a substantially ignorable level by suppressing the water content in the reaction liquid to a low level, for example, not higher than 5 weight %. In the case where the relationship a<b cannot be kept throughout the reaction, there are disadvantages in that the amount of side reaction products is increased to lower the conversion or selectivity.

Incidentally, the relationship a<b cannot necessarily be kept throughout the reaction just by simply rendering the molar amount of the charged raw alkylene oxide larger than the molar amount of the charged raw carboxylic acid (JP-B-000720/1994).

In addition, as is mentioned above, the production process according to the present invention is characterized in that the reaction is carried out in a reaction liquid under conditions where a relationship a<b is kept throughout the reaction wherein "a" is a molar concentration (mol %) of the carboxylic acid in the above reaction liquid and wherein "b" is a molar concentration (mol %) of the alkylene oxide in the above reaction liquid, but, in the case where the reaction is carried out in a batch manner, the above phrase "throughout the reaction" means "in the reaction step after the raw materials have been charged until their molar ratio reaches a set value". In addition, in the case where the reaction is carried out in a batch manner, it is preferable that the relationship between the molar concentration "a" (mol %) of the carboxylic acid in the reaction liquid and the molar concentration "b" (mol %) of the alkylene oxide in the reaction liquid is brought into the relationship a<b as soon as possible. Specifically, the ratio of the time of the addition of the whole alkylene oxide to the total reaction time (from the initiation of the addition of the alkylene oxide till the attainment of the conversion of the alkylene oxide or carboxylic acid to a set value) is preferably not more than 70%, more preferably not more than 60%, still more preferably not more than 50%.

A preferred mode of the present invention is that, as is mentioned above, the reaction is carried out in a reaction liquid under conditions where a relationship a<b is kept throughout the reaction wherein "a" is a molar concentration (mol %) of the carboxylic acid in the reaction liquid and wherein "b" is a molar concentration (mol %) of the alkylene oxide in the reaction liquid, but, as to this mode, it is more preferable that the reaction is continuously carried out while the conversion of the alkylene oxide is kept in the range of 10~98 mol % and while the conversion of the carboxylic acid is kept in the range of 70~99 mol %, and it is particularly preferable that the reaction is continuously carried out while the conversion of the alkylene oxide is kept in the range of 25~98 mol % and while the conversion of the carboxylic acid is kept in the range of 70~95 mol %. In the above mode, the raw materials may be added either continuously or intermittently. In the case where the conversion of the alkylene oxide is less than 10 mol % or where the conversion of the carboxylic acid is less than 70 mol %, a large amount of raw materials are uneconomically recovered. In addition, in the case where the conversion of the alkylene oxide is more than 98 mol % or where the conversion of the carboxylic acid is more than 99 mol %, a large amount of alkylene glycol dicarboxylate (hereinafter referred to as diester) is unfavorably formed.

In the present invention, furthermore, an unreacted residue of the alkylene oxide and/or an unreacted residue of the carboxylic acid may be recovered and then recycled as raw reaction materials for the hydroxyalkyl ester. If the unreacted recovered raw materials are recycled as raw reaction materials like this, then the production cost can be more lowered. Incidentally, the recovered unreacted raw materials may contain the hydroxyalkyl ester, and further, in view of the control of the generated reaction heat, the hydroxyalkyl ester may be mixed with the recovered raw materials and then added into the reactor. However, in the case where a large amount of hydroxyalkyl ester is added into the reactor, a large amount of by-products such as diesters are formed, therefore the amount of the hydroxyalkyl ester which is contained in the recovered raw materials is preferably not larger than 4.0 times, more preferably not larger than 2.0 times, still more preferably not larger than 1.0 time, by weight, of the total amount of recovered raw acid and freshly added raw acid.

The catalyst which is used for the reaction between the carboxylic acid and the alkylene oxide in the production process according to the present invention is not especially limited, but those which are used conventionally in this kind of reaction are usable. Specific examples thereof include at least one member selected from the group consisting of: iron compounds such as iron powder, ferric chloride, iron formate, ferric acetate, iron acrylate, and iron methacrylate; chromium compounds such as sodium bichromate, chromium chloride, chromium acetylacetonate, chromium formate, chromium acetate, chromium acrylate, chromium methacrylate, and chromium dibutyldithiocarbamate; and amines such as trialkylamines and ion-exchange resins having a quaternary ammonium group. However, among them, a basic resin is preferably used as the catalyst. This basic resin is a high molecular compound (e.g. molecular weight≧1,000) which has a basic functional group and is insoluble in the reaction liquid, for example, a high molecular compound having a basic functional group such as tertiary amine compounds, quaternary ammonium salts, cyclic amine compounds (e.g. pyridine), or sulfides, preferably, basic anion-exchange resins, particularly preferably, basic anion-exchange resins having an amino group as the basic functional group. In addition, the basic resin may be used jointly with such as the aforementioned iron compounds or chromium compounds.

It is preferable that the basic resin, which is preferably usable as the catalyst in the present invention, has a heat-resistant temperature of not lower than 70° C. Herein, the heat-resistant temperature is such as determined by the below-explained heat resistance test.

The heat-resistant temperature as determined by the heat resistance test is a temperature at which the exchange capacity of the resin decreases by not less than 20% when carrying out a process including the steps of: placing a water-humidified resin, of which the counter anion is an OH type, into a stainless (SUS316) autoclave; and then adding thereto acetic acid in an amount of 5 times as large as the volume of the resin; and then leaving the resultant mixture at a test temperature for 6 months under an atmosphere comprising oxygen 5% and nitrogen 95%.

In the case where the heat-resistant temperature is lower than 70° C., it is difficult that the reaction temperature conditions to sufficiently enhance the conversion or selectivity in the reaction are realized for a long period of time. In addition, in the case where a basic anion-exchange resin having a heat-resistant temperature lower than 70° C. and containing a trimethylammonium group is used as the basic resin to carry out the reaction under high-temperature reaction conditions, the elimination of the trimethylammonium group which acts as an active group in the reaction easily occurs, therefore the catalytic activity rapidly deteriorates with the passage of the reaction time. Furthermore, trimethylamine as derived from the basic anion-exchange resin mingles into the reaction product to contaminate the reaction product, so there are problems of such as color tone deterioration of the final product.

When the basic resin is used as the catalyst in the present invention, it is preferable that a water-humidified catalyst which is obtained by an immersion test of the catalyst as used cannot pass through a screen of 48 meshes (designation by Tyler: mesh opening size=297 μm) in a ratio of not less than 80 vol %, more preferably not less than 90 vol %, of what the water-humidified catalyst is before the test.

In other words, when the basic resin is used as the catalyst in the present invention, it is preferable that a water-humidified catalyst which is obtained by an immersion test of the catalyst as used can pass through a screen of 48 meshes (designation by Tyler: mesh opening size=297 μm) in a ratio of less than 20 vol %, more preferably less than 10 vol %, of what the water-humidified catalyst is before the test.

Herein, the immersion test is carried out by the following process. First, a water-humidified resin of which the counter anion is an OH type is charged into a resin cylinder, and then hydroxyethyl acrylate is allowed to flow down from the top of the resin cylinder to displace impregnated water in the resin by the hydroxyethyl acrylate. Next, this resin is transferred into a stainless autoclave, to which hydroxyethyl acrylate is then added in an amount of 2 times as large as the amount of the resin. Then, after they are heated to 90° C. while being stirred to such an extent that the temperature of the liquid can be uniform, water is added all at once in an amount of 5 times as large as the amount of the resin. After the resultant solution is cooled, the resin is separated therefrom and then charged into a resin cylinder. Then, water is allowed to flow down from the top of the resin cylinder to displace impregnated hydroxyethyl acrylate in the resin by the water. The resultant resin is sieved with a screen of 48 meshes (designation by Tyler: mesh opening size=297 μm) to measure the ratio of fractions, not passing through this screen, of the resin (or the ratio of fractions, passing through this screen, of the resin). In this process, a polymerization inhibitor is fitly used to inhibit the polymerization of the hydroxyethyl acrylate.

If the water-humidified catalyst which is obtained by the immersion test cannot pass through the screen of 48 meshes (designation by Tyler: mesh opening size=297 μm) in a ratio of not less than 80 vol % of what the water-humidified catalyst is before the test, then there are advantages in that problems of cracking or fracture of the catalyst do not occur when the catalyst is used for a long period of time. In the case where the catalyst cannot pass through the screen of 48 meshes (designation by Tyler: mesh opening size=297 μm) in a ratio of less than 80 vol % of what the water-humidified catalyst is before the test, there are disadvantages as follows: the problems of cracking or fracture of the catalyst occur when the catalyst is used for a long period of time, therefore blocking by the catalyst occurs so easily as to deteriorate the reaction activity; in addition, in the case where the catalyst is used in a state filled in the reaction tube, the pressure loss is so large as to deteriorate the liquid permeability; on the other hand, in the case where the catalyst is used in a tank reactor as equipped with a stirrer, the catalyst adheres to a wall face of the reactor, therefore the catalyst is lost to deteriorate the reaction activity.

When the basic resin is used as the catalyst in the present invention, it is preferable that a water-humidified catalyst which is obtained by an abrasion test of the catalyst as used cannot pass through a screen of 48 meshes (designation by Tyler: mesh opening size=297 μm) in a ratio of not less than 80 vol %, more preferably not less than 90 vol %, of what the water-humidified catalyst is before the test.

Herein, the abrasion test is carried out by the following process. First, 300 ml of a water-humidified resin of which the counter anion is a Cl type is charged together with 300 ml of water into a SUS316-made autoclave of 2 liters in capacity (inner diameter: 120 mm) as equipped with a stirrer. The contents of the autoclave are stirred at room temperature at 900 rpm for 15 hours with six flat-plate blades (non-tilted, made of SUS316, blade diameter 85 mm, blade height 15 mm) used as the stirring blades, when an appropriate inner lid is set at an upper part near the liquid level so that the resin may not scatter onto the wall face or lid portion. Then, the resin is separated and then sieved with a screen of 48 meshes (designation by Tyler: mesh opening size=297 μm) to measure the ratio of fractions, not passing through this screen, of the resin.

If the water-humidified catalyst which is obtained by the abrasion test cannot pass through the screen of 48 meshes (designation by Tyler: mesh opening size=297 μm) in a ratio of not less than 80 vol % of what the water-humidified catalyst is before the test, then there are advantages in that problems of abrasion or fracture of the catalyst do not occur when the catalyst is used for a long period of time. In the case where the catalyst cannot pass through the screen of 48 meshes (designation by Tyler: mesh opening size=297 μm) in a ratio of less than 80 vol % of what the water-humidified catalyst is before the test, there are disadvantages as follows: the reaction activity is deteriorated due to the abrasion of the catalyst when the catalyst is used for a long period of time; and further, abraded pieces of the catalyst are brought to subsequent steps, therefore clogging up the piping, or forming by-products in the purification step.

It is preferable that the basic resin, which is preferably usable as the catalyst in the present invention, has an average particle diameter in the range of 300~5,000 μm.

In the case where the above average particle diameter is out of the range of 300~5,000 μm, there are disadvantages, specifically, in the case where the above average particle diameter is smaller than 300 μm, the reaction activity is deteriorated similarly to the aforementioned and, in the case where the above average particle diameter is larger than 5,000 μm, the reaction activity is deteriorated due to the decrease of the surface area of the resin. The average particle diameter is more preferably in the range of 400~2,000 μm.

Incidentally, the average particle diameter or size of the resin is measured in accordance with Manual of DIAION Ion-Exchange Resins, Synthetic Adsorbent (published by Mitsubishi Chemical Corporation).

It is preferable that the basic resin, which is preferably usable as the catalyst in the present invention, is such that the ratio of a cracked resin in a solvent-swollen catalyst which is obtained by a solvent displacement test of the basic resin is not more than 50%.

Herein, the solvent displacement test is carried out by the following process. A water-humidified resin of which the counter anion is an OH type is placed into a container, to which acrylic acid is then added in an amount of 5 times as large as the amount of the resin, and the resultant mixture is stirred with a stirring rod for several minutes. After being separated from the liquid with filter paper, the resin is placed into a container again, to which water is then added in an amount of 5 times as large as the amount of the resin, and the resultant mixture is stirred with a stirring rod for several minutes. After the resin is separated from the liquid with filter paper, 500 pieces of the resin are observed with an optical microscope (magnifications: 25) to count the number of resin pieces having cracks or flaws (referred to as cracked resin), thus measuring the ratio of the cracked resin.

If the above ratio of the cracked resin is not more than 50%, then there are advantages in that problems of cracking or fracture of the resin due to the deterioration of the strength of the resin do not occur when the resin is used for a long period of time. In the case where the above ratio of the cracked resin is more than 50%, problems of cracking, fracture, or powdering of the resin occur due to the use of the resin for a long period of time, therefore the reaction activity is deteriorated similarly to the aforementioned case of the immersion test. In addition, usually, before the initiation of the reaction, an impregnated liquid in the resin which is a catalyst is displaced with the raw acid or product hydroxyalkyl ester and their mixture (in the case of dry resin, it is humidified), when the resin swells or shrinks, then, in the case where the ratio of the cracked resin in this solvent displacement test is more than 50%, the resin might fracture.

It is preferable that the catalyst, which is used in the present invention, is a basic anion-exchange resin, and has an ion-exchange capacity of not less than 2.0 meq/g-dry (OH type) and a water content of not less than 40 weight % (OH type).

The ion-exchange capacity is an exchange capacity per unit weight of dry resin, and is measured in accordance with Manual of DIAION Ion-Exchange Resins, Synthetic Adsorbent (published by Mitsubishi Chemical Corporation).

The water content is a weight ratio of water in unit water-containing resin, and is measured in accordance with Manual of DIAION Ion-Exchange Resins, Synthetic Adsorbent (published by Mitsubishi Chemical Corporation).

In the case where the ion-exchange capacity is less than 2.0 meq/g-dry (OH type), sufficient catalytic activity is not obtained. Furthermore, in the case where the water content is less than 40 weight % (OH type), the resin does not sufficiently swell, therefore it is difficult to expect high activity.

The amount of the above catalyst, which is used for carrying out the present invention, is not especially limited, but, in the case where the catalyst is a heterogeneous catalyst and where the reaction is run in a batch manner, the catalyst is usually used in the range of 5~50 weight %, particularly preferably 10~30 weight %, of the raw carboxylic acid. In addition, in the case where the reaction is a continuous one and where the catalyst is used in the fluidized bed manner with such as tank reactor, the catalyst is used in the range of usually 30~90 vol %, preferably 50~80 vol %, of the reaction liquid. In addition, in the case where the catalyst is used in the fixed bed manner with such as tubular reactor, a liquid which contains raw materials for the reaction is allowed to pass through at a liquid hourly space velocity (LHSV: $h^{-1}$) of preferably 0.05~15, more preferably 0.2~8. On the other hand, in the case where the catalyst is a homogeneous catalyst, the catalyst is usually used in the range of 0.05~10 weight %, particularly preferably 0.1~3 weight %, of the raw carboxylic acid.

Next, specific modes for carrying out the production process according to the present invention are described on the basis of FIGS. 1~5. However, the production process according to the present invention is not limited to these modes.

Figure 2:
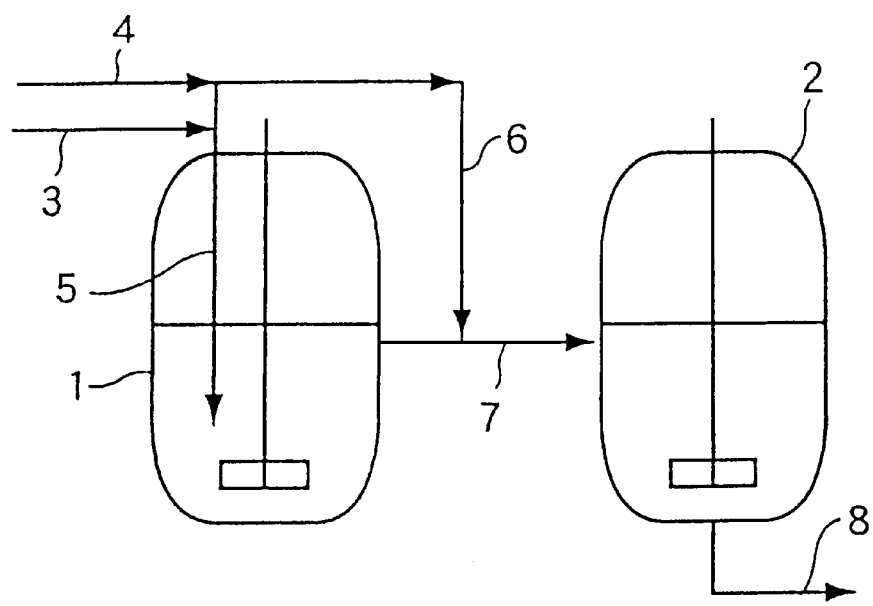
FIG. 2 is an illustration of another mode for carrying out the present invention in which two tank reactors are used.
Figure 3:
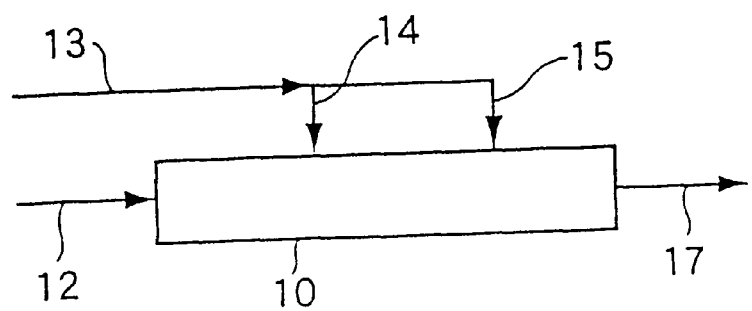
FIG. 3 is an illustration of another mode for carrying out the present invention in which a single tubular reactor is used.
Figure 4:
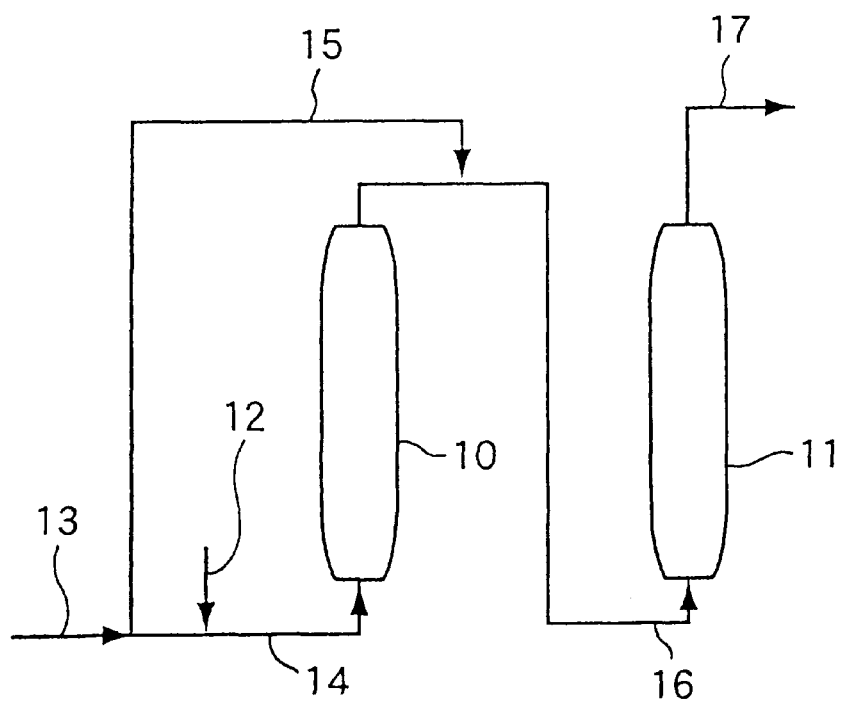
FIG. 4 is an illustration of another mode for carrying out the present invention in which two tubular reactors are used.
Figure 5:
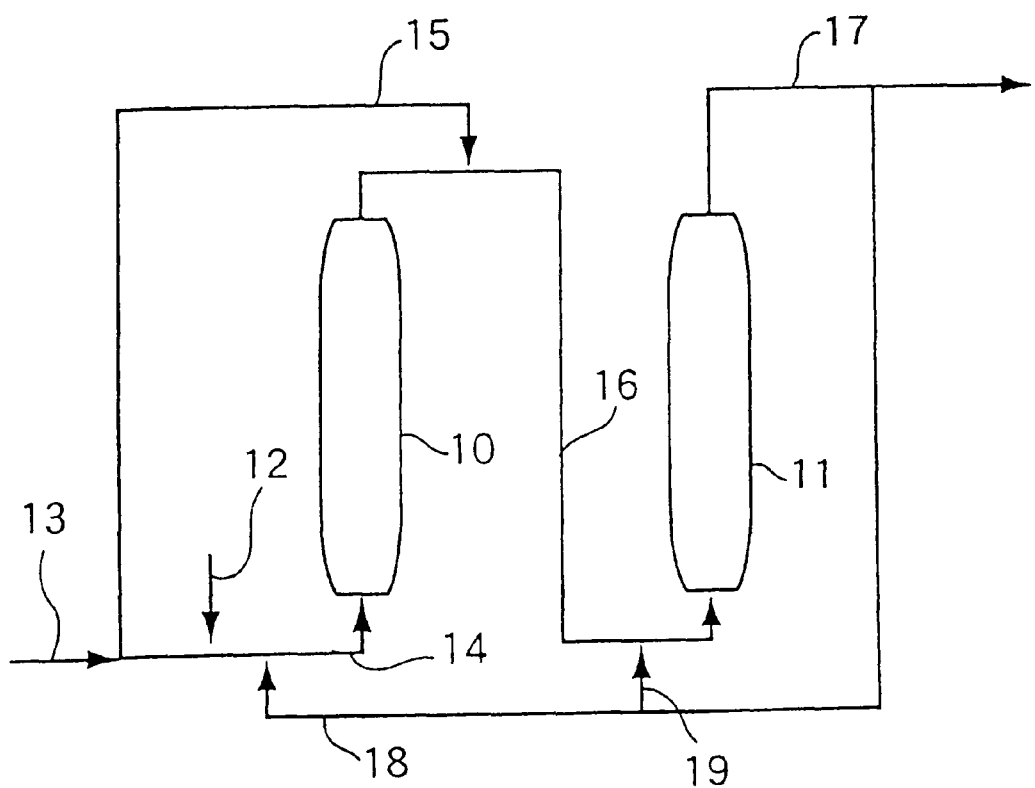
FIG. 5 is an illustration of another mode for carrying out the present invention in which a part of reaction liquid is circulated.

FIG. 1 is an illustration of one mode for carrying out the present invention in which a single tank reactor is used. FIG. 2 is an illustration of another mode for carrying out the present invention in which two tank reactors are used. FIG. 3 is an illustration of another mode for carrying out the present invention in which a single tubular reactor is used. FIG. 4 is an illustration of another mode for carrying out the present invention in which two tubular reactors are used. In addition, FIG. 5 is an illustration of a mode in which a part of reaction liquid is circulated in the mode as shown in FIG. 4. Hereinafter, on the basis of FIGS. 1~5, the present invention is described in detail.

In FIG. 1, the alkylene oxide and the carboxylic acid are introduced from lines 3 and 4 respectively into a tank reactor 1. After the end of the reaction, the resultant reaction liquid containing the hydroxyalkyl ester which is the aimed product is extracted from a line 8.

The reaction in which the tank reactor of FIG. 1 is used can be carried out in accordance with various modes. For example, the whole alkylene oxide is beforehand charged into the reactor 1, and then the carboxylic acid is continuously introduced little by little from the line 4 (mode (1)). In addition, the whole alkylene oxide is beforehand charged into the reactor 1, and the carboxylic acid is divided into at least two which are then introduced one after another from the line 4 (mode (2)). Furthermore, a part of the carboxylic acid is beforehand charged into the reactor 1, and thee the whole alkylene oxide is supplied thereto, and then the rest of the carboxylic acid is introduced from the line 4 (after further divided as the case may be) (mode (3)).

Accordingly, the "steps of dividing the carboxylic acid into at least two and then supplying them" in the modes for carrying out the present invention encompass the above mode (1) in which a single tank reactor is used.

Incidentally, for rendering the residence time of the carboxylic acid in the reaction system as short as possible, it is preferable in the mode (1) that the carboxylic acid is supplied as little by little as possible. In addition, as to the modes (2) and (3), it is preferable that the number of the divisions of the carboxylic acid is as large as possible, but it is enough to supply 2~10 divisions, preferably 2~4 divisions.

The above mode (3) is explained in detail as follows. The catalyst and half the whole carboxylic acid to be charged are charged into the reactor 1 as equipped with a stirrer and a heating and radiating jacket. Next, while the stirrer is rotated, the whole alkylene oxide to be charged is added into the reactor, when the reaction runs in some degree to generate a reaction heat, therefore this heat is radiated from the jacket or the amount of the alkylene oxide as added is adjusted, thereby keeping the liquid temperature constant. After the addition of the alkylene oxide has been completed, the liquid temperature is gradually raised to a set temperature. After the temperature raising has been completed, the reaction is run while the heat is radiated to keep this temperature. When, for example, 80 weight % of the charged carboxylic acid has reacted, $2/3$ of the rest of the carboxylic acid is added. Thereafter, the reaction is run while the heat is radiated to keep the reaction temperature. Next, when, for example, 80 weight % of the already charged carboxylic acid has reacted, the rest of the carboxylic acid is added, and then, when the total conversion of the carboxylic acid has reached a set value, the reaction is ended.

In the case where the carboxylic acid is divided into two in the mode for carrying out the present invention as shown in FIG. 1, it is preferable that the amount of the carboxylic acid as introduced at the first time is not smaller than $1/2$, more preferably in the range of $1/2$~$9/10$, of the whole carboxylic acid, and that the rest is introduced at the second time. In the case where the carboxylic acid is divided into three, it is preferable that the amount of the carboxylic acid as introduced at the first time is not smaller than $1/3$, more preferably in the range of $1/3$~$9/10$, of the whole carboxylic acid, and that the amount of the carboxylic acid as introduced at the second time is not smaller than $1/2$, more preferably in the range of ½~9/10, of the rest of the carboxylic acid, but is smaller than the amount of the carboxylic acid as introduced at the first time, and further that the amount of the carboxylic acid as introduced at the third time is smaller than the amount of the carboxylic acid as introduced at the second time. Also in the case where the carboxylic acid is divided into four, it is preferable that this division into four is carried out in the same way as of the above division into two or three.

In FIG. 2, two tank reactors 1 and 2 are used to continuously carry out the reaction. First, as to the reactor 1, the reaction is carried out by introducing the alkylene oxide from a line 3 through a line 5 from which a part of the carboxylic acid from a line 4 is introduced. Next, the resultant reaction liquid is introduced into the reactor 2 through a line 7, when the rest of the carboxylic acid is introduced from a line 6 into the reactor 2, thus further running the reaction. Then, the resultant reaction liquid containing the hydroxyalkyl ester which is the aimed product is extracted from a line 8.

In the case where more than one tank reactor is used to continuously carry out the reaction, the number of the reactors is preferably in the range of 2~10, more preferably 2~4, in view of the apparatus cost. Incidentally, the step of dividing the carboxylic acid is preferably such that the carboxylic acid is divided in the same way as explained about the above mode for carrying out the present invention as shown in FIG. 1, and then introduced into each reactor.

The continuous reaction in which the two reactors of FIG. 2 are used can be carried out in accordance with various modes, one of which is explained in detail as follows. A catalyst (e.g. ion-exchange resin having a quaternary ammonium group) which is insoluble in the reaction liquid is filled in a predetermined concentration into two reactors 1 and 2 as equipped with a stirrer and a heating and cooling jacket. Then, the whole alkylene oxide to be charged and 75 weight % of the whole carboxylic acid to be charged are continuously supplied into the reactor 1 to carry out the reaction. Next, the catalyst is removed from the resultant reaction liquid, which is then supplied from the reactor 1 through the line 7 into the reactor 2, when the residual 25 weight % of the carboxylic acid is supplied into the line 7. Then, after being separated from the catalyst, the resultant reaction liquid containing the hydroxyalkyl ester which is the aimed product is extracted from the line 8 of the reactor 2.

In FIG. 3, a single tubular reactor is used to continuously carry out the reaction. Specifically, the alkylene oxide is introduced from a line 12 into a tubular reactor 10, and the carboxylic acid as supplied from a line 13 is divided into two which are then introduced from lines 14 and 15 respectively into the reactor 10. Then, the resultant reaction liquid containing the hydroxyalkyl ester which is the aimed product is extracted from a line 17.

The step of dividing the carboxylic acid is the same as explained about the above modes for carrying out the present invention as shown in FIGS. 1 and 2. Incidentally, the position where the divided carboxylic acid is introduced into the tubular reactor is not especially limited, but can fitly be determined.

In FIG. 4, two tubular reactors 10 and 11 are used to continuously carry out the reaction. Specifically, as to the reactor 10, the whole alkylene oxide is introduced from a line 12 into the reactor 10, and the carboxylic acid as supplied from a line 13 is divided into two, one of which is then introduced from a line 14 into the reactor 10. Next, a reaction liquid resultant from the reactor 10 is introduced through a line 16 into the reactor 11, when the rest of the carboxylic acid is introduced from a line 15 into the reactor 11.

The step of dividing the carboxylic acid is the same as explained about the above modes for carrying out the present invention as shown in FIGS. 1 and 2. The number of the tubular reactors is usually in the range of 2~4.

The continuous reaction in which the two reactors of FIG. 4 are used can be carried out in accordance with various modes, one of which is explained in detail as follows. A catalyst (e.g. ion-exchange resin having a quaternary ammonium group) which is insoluble in the reaction liquid is filled into tower type tubular reactors 10 and 11 (at both ends of which a filter is set) as equipped with a heating and cooling jacket. Then, the whole alkylene oxide to be charged and 75 weight % of the whole carboxylic acid to be charged are mixed together in the line 14, and the resultant mixture is continuously supplied into the reactor 10 in a up-flow. Next, a reaction liquid resultant from the reactor 10 is supplied through the line 16 into the reactor 11, when the residual 25 weight % of the carboxylic acid is added from the line 15 and then mixed into the reaction liquid in the line 16, and the resultant mixture is supplied into the reactor 11. Then, the resultant reaction liquid containing the hydroxyalkyl ester which is the aimed product is extracted from a line 17 of the reactor 11.

FIG. 5 is an illustration of a mode in which a part of the reaction liquid from the line 17 is circulated through lines 18 and 19 into the reactors 10 and 11 respectively. Thus, in the present invention, a part of the reaction liquid from the line 17, or the residue as produced by removing the hydroxyalkyl ester (aimed product) from the reaction liquid, may be circulated into the reactors 10 and/or 11 to cause unreacted materials in the reaction liquid to react again. For example, an unreacted residue of the carboxylic acid may be separated from the reaction liquid and then circulated into the reactors 10 and/or 11. Or it is permissible that fresh raw carboxylic acid only is introduced into the reactor 10, while recovered carboxylic acid (unreacted carboxylic acid) only is introduced into the reactor 11. Furthermore, it is permissible that: the recovered carboxylic acid and the fresh carboxylic acid are once mixed together, and then the resultant mixture is divided and then added into each reactor.

In the present invention, as the need arises, the resultant crude hydroxyalkyl ester may further be purified. The purification method is not especially limited, but examples thereof include purification by distillation, specifically, distillation involving the use of such as conventional distillation columns or rectifying columns (e.g. packed columns, bubble cap columns, perforated-plate columns), but there is no especial limitation thereto. In addition, other purification means may be used jointly with the distillation purification.

As is mentioned above, in the present invention, the reaction is carried out in a state where the alkylene oxide is excessive to the carboxylic acid throughout the reaction. This state where the alkylene oxide is excessive is preferably kept throughout the reaction, in other words, in the whole reaction process, but, in the present invention, it is enough that the state where the alkylene oxide is excessive is kept in the substantially whole reaction process. Therefore, like in the case where a plurality of reactors are used, the state where the alkylene oxide is excessive does not need to be kept up to in the final reactor in which the reaction has substantially reached a prescribed stage.

(Effects and Advantages of the Invention)

The present invention provides a production process for a hydroxyalkyl ester which comprises the step of carrying out a reaction between a carboxylic acid and an alkylene oxide, wherein the production process can sufficiently enhance the conversion or selectivity in the reaction. Furthermore, this production process can effectively inhibit the formation of by-products such as alkylene glycol diesters and dialkylene glycol monoesters.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to these examples.

Production Example 1

Synthesis of Anion-exchange Resin

Synthesis of 4-bromobutoxymethylstyrene

An amount of 20 g (0.5 mol) of sodium hydroxide and 20 ml of water were placed into a four-necked flask of 300 ml in capacity and then stirred to prepare a homogeneous solution. The temperature of this solution was reverted to room temperature, and then thereto a solution as prepared by dissolving 13.42 g (0.1 mol) of vinylbenzyl alcohol (mixture of m-isomer and p-isomer), 32.39 g (0.15 mol) of 1,4-dibromobutane, and 3.22 g (0.01 mol) of tetrabutylammonium bromide into 100 ml of toluene was added. While being vigorously stirred, the resultant mixed solution was allowed to react at 40° C. for 6 hours. Thereafter, the solution was separated and then sufficiently washed with water. The resultant organic layer was dried by adding thereto magnesium sulfate, and then toluene was distilled off under reduced pressure. The resultant solution was distilled in the presence of DPPH (diphenylpicryl-2-hydrazyl) under vacuum (boiling point: 125~128° C./16 Pa) to obtain a colorless transparent liquid of 4-bromobutoxymethylstyrene. The yield amount was 15.0 g, and the yield ratio was 56 mol %.

Synthesis of Anion-exchange Resin

An amount of 200 ml of desalted water and 50 ml of 2 weight % aqueous poly(vinyl alcohol) solution were placed into a four-necked flask of 500 ml in capacity as equipped with a nitrogen-gas-introducing tube and a condenser, and then nitrogen gas was introduced into the resultant water layer to remove dissolved oxygen therefrom. On the other hand, a monomer layer, in which 46.4 g of 4-bromobutoxymethylstyrene, 1.72 g of divinylbenzene (industrial one, purity 56 weight %), and 0.4 g of AIBN were dissolved, was prepared. Then, dissolved oxygen was remove from the monomer layer in the same way as of the above water layer. The resultant monomer solution was added into the flask, and then the resultant mixture was stirred at 150 rpm to form liquid drops of the monomers. The mixture was stirred at room temperature for 30 minutes and then further stirred at 70° C. for 18 hours. After the polymerization, the resultant polymer was separated, and then this resin was washed with water, and then further washed with methanol three times. As a result, a light-yellow transparent spherical resin was obtained in a polymerization yield of 93% and a charge-crosslinking degree of 4 mol %.

Next, the above resin was placed into a four-necked flask of 500 ml in capacity having a condenser, and then 500 ml of methanol was added to the resin, and then they were stirred at room temperature. Then, 200 ml of 30 weight % aqueous trimethylamine solution was added to the resultant solution to carry out a reaction at 50° C. for 10 hours to introduce a trimethylammonium group. After the reaction, the resultant polymer was separated and then sufficiently washed with water. For the purpose of converting a counter ion of this anion-exchange resin from bromide ion into chloride ion (Cl form), a 4 weight % aqueous sodium chloride solution was run through the resin in an amount of 10 times as large as the amount of the resin. The below-mentioned properties of the resultant Cl form of resin were measured. Incidentally, its average particle diameter was 750 μm.

| | |
|---|---|
| Neutral salt decomposition capacity: | 3.42 meq/g (0.832 meq/ml) |
| Water content: | 57.0 weight % |
| Heat-resistant temperature | 80° C. |

Incidentally, the above properties were measured in accordance with Manual of DIAION Ion-Exchange Resins, Synthetic Adsorbent (published by Mitsubishi Chemical Corporation). However, the heat-resistant temperature was measured by the method as described herein.

Example 1

An autoclave of 1 liter in capacity, as equipped with a thermometer, a heating and cooling unit, a safety valve, and a stirrer, was charged with 400 ml of a water-humidified basic anion-exchange resin (which was obtained in Production Example 1 and had an average particle diameter of 590 μm as adjusted by sieving, and which did not pass through a screen of 48 meshes (designation by Tyler: mesh opening size=297 μm) in a ratio of 98 vol % (which passed through this screen in a ratio of 2 vol %) after the immersion test, and further, which did not pass through a screen of 48 meshes (designation by Tyler: mesh opening size=297 μm) in a ratio of 98 vol % after the abrasion test) as a catalyst, 5 g of hydroquinone monomethyl ether as a polymerization inhibitor, and acrylic acid to prepare a total amount of 600 ml of mixture. The resultant mixture was heated to 70° C., and then air in the autoclave was replaced with nitrogen gas. Thereafter, ethylene oxide and acrylic acid (containing hydroquinone monomethyl ether in a ratio of 1.0 weight %) were continuously supplied into the autoclave at rates of 101 g/h and 109 g/h respectively (ethylene oxide/acrylic acid= 1.5 (molar ratio)). The resultant reaction liquid was continuously extracted such that the liquid level in the autoclave could be fixed during the reaction.

The reaction liquid as obtained in a stationary state was analyzed by gas chromatography. The results are as follows:

| | |
|---|---|
| Conversion of acrylic acid: | 86 mol % |
| Conversion of ethylene oxide: | 58 mol % |
| Molar ratio of ethylene oxide/acrylic acid: | 4.7 |
| Selectivity of diethylene glycol monoacrylate (based on the conversion of acrylic acid; hereinafter the same): | 1.7 mol % |
| Selectivity of diester (based on the conversion of acrylic acid; hereinafter the same): | 0.18 mol % |

In addition, coloring of the reaction liquid was not seen.

Example 2

Two autoclaves of 1 liter in capacity, which were the same as that used in Example 1, were used, and further, a water-humidified basic anion-exchange resin which was the same as that used in Example 1, in other words, which was obtained in Production Example 1, was used as the catalyst. The first autoclave was charged with 400 ml of the resin, 5 g of hydroquinone monomethyl ether as a polymerization inhibitor, and acrylic acid to prepare a total amount of 600 ml of mixture, while the second autoclave was charged with 320 ml of the resin, 5 g of hydroquinone monomethyl ether as a polymerization inhibitor, and acrylic acid to prepare a total amount of 480 ml of mixture. The resultant mixtures were heated to 70° C., and then air in the autoclaves was replaced with nitrogen gas. Into the first autoclave, ethylene oxide and acrylic acid (containing hydroquinone monomethyl ether in a ratio of 1.0 weight %) were continuously supplied at rates of 101 g/h and 109 g/h respectively (ethylene oxide/acrylic acid=1.5 (molar ratio)) in the same way as of Example 1. The resultant reaction liquid was continuously extracted such that the liquid level in the autoclave could be fixed during the reaction. Into the second autoclave, this extracted reaction liquid and acrylic acid (containing hydroquinone monomethyl ether in a ratio of 1.0 weight %) (41 g/h) were supplied. The resultant reaction liquid was continuously extracted such that the liquid level in the autoclave could be fixed during the reaction.

The reaction liquids as obtained in a stationary state were analyzed by gas chromatography. As to the liquid as discharged from the outlet of the first autoclave, the results are as follows:

| | |
|---|---|
| Conversion of acrylic acid: | 86 mol % |
| Conversion of ethylene oxide: | 58 mol % |
| Molar ratio of ethylene oxide/acrylic acid: | 4.7 |
| Selectivity of diethylene glycol monoacrylate: | 1.7 mol % |
| Selectivity of diester: | 0.18 mol % |

As to the liquid as discharged from the outlet of the second autoclave, the results are as follows:

| | |
|---|---|
| Conversion of acrylic acid: | 83 mol % |
| Conversion of ethylene oxide: | 76 mol % |
| Molar ratio of ethylene oxide/acrylic acid: | 1.6 |
| Selectivity of diethylene glycol monoacrylate: | 1.7 mol % |
| Selectivity of diester: | 0.21 mol % |

In addition, coloring of the reaction liquid was not seen.

Comparative Example 1

A autoclave of 1 liter in capacity, which was the same as that used in Example 1, was charged with 400 ml of a water-humidified basic anion-exchange resin (which was the same as that used in Example 1, in other words, which was obtained in Production Example 1) as a catalyst, 5 g of hydroquinone monomethyl ether as a polymerization inhibitor, and acrylic acid to prepare a total amount of 600 ml of mixture. The resultant mixture was heated to 70° C., and then air in the autoclave was replaced with nitrogen gas. Thereafter, ethylene oxide and acrylic acid (containing hydroquinone monomethyl ether in a ratio of 1.0 weight %) were continuously supplied into the autoclave at rates of 82 g/h and 133 g/h respectively (ethylene oxide/acrylic acid=1.01 (molar ratio)). The resultant reaction liquid was continuously extracted such that the liquid level in the autoclave could be fixed during the reaction.

The reaction liquid as obtained in a stationary state was analyzed by gas chromatography. The results are as follows:

| | |
|---|---|
| Conversion of acrylic acid: | 63 mol % |
| Conversion of ethylene oxide: | 65 mol % |
| Molar ratio of ethylene oxide/acrylic acid: | 0.95 |
| Selectivity of diethylene glycol monoacrylate: | 3.7 mol % |
| Selectivity of diester: | 0.56 mol % |

Coloring of the reaction liquid was not seen, but it was found that the ratio of the addition of raw materials was lower than that in Example 1, and further that the selectivity of the diethylene glycol monoacrylate and the selectivity of the diester were higher than those in Example 1.

Example 3

A autoclave of 1 liter in capacity, which was the same as that used in Example 1, was charged with 400 ml of a water-humidified basic anion-exchange resin (which was the same as that used in Example 1, in other words, which was obtained in Production Example 1) as a catalyst, 5 g of hydroquinone monomethyl ether as a polymerization inhibitor, and acrylic acid to prepare a total amount of 600 ml of mixture. The resultant mixture was heated to 70° C., and then air in the autoclave was replaced with nitrogen gas. Thereafter, ethylene oxide and acrylic acid (containing hydroquinone monomethyl ether in a ratio of 1.0 weight %) were continuously supplied into the autoclave at rates of 187 g/h and 236 g/h respectively (ethylene oxide/acrylic acid=1.3 (molar ratio)). The resultant reaction liquid was continuously extracted such that the liquid level in the autoclave could be fixed during the reaction.

The reaction liquid as obtained in a stationary state was analyzed by gas chromatography. The results are as follows:

| | |
|---|---|
| Conversion of acrylic acid: | 67 mol % |
| Conversion of ethylene oxide: | 52 mol % |
| Molar ratio of ethylene oxide/acrylic acid: | 1.9 |
| Selectivity of diethylene glycol monoacrylate: | 1.6 mol % |
| Selectivity of diester: | 0.15 mol % |

In addition, coloring of the reaction liquid was not seen.

Example 4

An autoclave of 1 liter in capacity, which was the same as that used in Example 1, was charged with 400 ml of a water-humidified basic anion-exchange resin SA10A (produced by Mitsubishi Chemicals Corporation; heat-resistant temperature=60° C.; average particle diameter=490 μm; which did not pass through a screen of 48 meshes (designation by Tyler: mesh opening size=297 μm) in a ratio of 98 vol % (which passed through this screen in a ratio of 2 vol %) after the immersion test, and further, which did not pass through a screen of 48 meshes (designation by Tyler: mesh opening size=297 μm) in a ratio of 93 vol % after the abrasion test) as a catalyst, 5 g of hydroquinone monomethyl ether as a polymerization inhibitor, and acrylic acid to prepare a total amount of 600 ml of mixture. The resultant mixture was heated to 70° C., and then air in the autoclave was replaced with nitrogen gas. Thereafter, ethylene oxide and acrylic acid (containing hydroquinone monomethyl ether in a ratio of 1.0 weight %) were continuously supplied into the autoclave at rates of 101 g/h and 109 g/h respectively (ethylene oxide/acrylic acid=1.5 (molar ratio)). The resultant reaction liquid was continuously extracted such that the liquid level in the autoclave could be fixed during the reaction.

The reaction liquid as obtained in a stationary state was analyzed by gas chromatography. The results are as follows:

| | |
|---|---|
| Conversion of acrylic acid: | 80 mol % |
| Conversion of ethylene oxide: | 53 mol % |
| Molar ratio of ethylene oxide/acrylic acid: | 3.5 |
| Selectivity of diethylene glycol monoacrylate: | 1.6 mol % |
| Selectivity of diester: | 0.18 mol % |

The result was that only a little yellow coloring of the reaction liquid was seen, but that the selectivity of the diethylene glycol monoacrylate and the selectivity of the diester were both low.

Example 5

A SUS316-made reaction tube (inner diameter: 8 mm, length: 10 m) was filled with a water-humidified anion-exchange resin PA316 (produced by Mitsubishi: Chemicals Corporation; heat-resistant temperature=60° C.; average particle diameter 750 μm; which did not pass through a screen of 48 meshes (designation by Tyler: mesh opening size=297 μm) in a ratio of 98.5 vol % (which passed through this screen in a ratio of 1.5 vol %) after the immersion test, and further, which did not pass through a screen of 48 meshes (designation by Tyler: mesh opening size=297 μm) in a ratio of 92 vol % after the abrasion test), and then a SUS316-made wire gauze was set at both ends of the reaction tube such that the resin could not flow out of the system. In addition, a back pressure valve was installed onto an upper end (on the outlet side) of this reaction tube to keep the internal pressure of the reaction tube at about 0.7 MPa, and then this reaction tube was immersed into an oil bath of 70° C. Next, ethylene oxide and acrylic acid (containing hydroquinone monomethyl ether in a ratio of 1.0 weight %) (ethylene oxide/acrylic acid=1.05 (molar ratio)) were then supplied to the reaction tube at a linear rate of 4 m/h with a proportioning pump, wherein the acrylic acid was divided into two to add 75 weight % of the acrylic acid into an inlet of the reaction tube and the residual 25 weight % into a distance of 2.5 m from the inlet of the reaction tube.

After continuing to run the liquid until the composition at the outlet of the reaction tube became constant, the reaction product flowing out of the outlet of the reaction tube was analyzed by gas chromatography. The results are as follows:

| | |
|---|---|
| Conversion of acrylic acid: | 87 mol % |
| Conversion of ethylene oxide: | 82 mol % |
| Molar ratio of ethylene oxide/acrylic acid: | 2.3 |
| Selectivity of diethylene glycol monoacrylate: | 1.4 mol % |
| Selectivity of diester: | 0.24 mol % |

The result was that only a little coloring of the reaction liquid was seen, but that the selectivity of the diethylene glycol monoacrylate and the selectivity of the diester were both low.

Example 6

The reaction was carried out in the same way as of Example 5 except that the acrylic acid was divided into three to add 55 weight % of the acrylic acid into the inlet of the reaction tube and the residual 30 weight % and 15 weight % into distances of 2.5 m and 5.0 m respectively from the inlet of the reaction tube.

After continuing to run the liquid until the composition at the outlet of the reaction tube became constant, the reaction product flowing out of the outlet of the reaction tube was analyzed by gas chromatography. The results are as follows:

| | |
|---|---|
| Conversion of acrylic acid: | 89 mol % |
| Conversion of ethylene oxide: | 84 mol % |
| Molar ratio of ethylene oxide/acrylic acid: | 2.4 |
| Selectivity of diethylene glycol monoacrylate: | 1.3 mol % |
| Selectivity of diester: | 0.20 mol % |

The result was that only a little coloring of the reaction liquid was seen, but that the selectivity of the diethylene glycol monoacrylate and the selectivity of the diester were both low.

Example 7

The reaction was carried out in the same way as of Example 5 except that the whole acrylic acid was introduced into the inlet of the reaction tube without being divided.

After continuing to run the liquid until the composition at the outlet of the reaction tube became constant, the reaction product flowing out of the outlet of the reaction tube was analyzed by gas chromatography. The results are as follows:

| | |
|---|---|
| Conversion of acrylic acid: | 75 mol % |
| Conversion of ethylene oxide: | 72 mol % |
| Molar ratio of ethylene oxide/acrylic acid: | 1.8 |
| Selectivity of diethylene glycol monoacrylate: | 2.6 mol % |
| Selectivity of diester: | 0.40 mol % |

The result was that only a little coloring of the reaction liquid was seen, but that the selectivity of the diethylene glycol monoacrylate and the selectivity of the diester were both low.

Example 8

Two autoclaves of 2 liters in capacity as equipped with a thermometer, a heating and cooling unit, and a stirrer were used as reactors, each of which was charged with 370 g of a water-humidified anion-exchange resin PA316 (DIAION produced by Mitsubishi Chemical Corporation) as a catalyst, 428 g of acrylic acid, and 5 g of hydroquinone monomethyl ether, and then heated to 70° C. Air in each reactor was replaced with nitrogen. Ethylene oxide and acrylic acid (containing hydroquinone monomethyl ether in a ratio of 1.0 weight %) were then supplied in a molar ratio (ethylene oxide/acrylic acid) of 1.1, wherein the acrylic acid was divided into two to introduce 75 weight % of the acrylic acid into the first reactor together with the whole ethylene oxide (4 mols/hour) and supply the residual 25 weight % into the second reactor, continuously with a proportioning pump. The resultant reaction liquid was continuously extracted such that the liquid level in each reactor could be fixed during the reaction.

After continuing to supply the ethylene oxide and the acrylic acid until the composition at the outlet of the second reactor became constant, the reaction product flowing out of the outlet of the second reactor was analyzed by gas chromatography. The results are as follows:

| | |
|---|---|
| Conversion of acrylic acid: | 88 mol % |
| Conversion of ethylene oxide: | 80 mol % |
| Molar ratio of ethylene oxide/acrylic acid: | 2.8 |
| Selectivity of diethylene glycol monoacrylate: | 1.6 mol % |
| Selectivity of diester: | 0.23 mol % |

The result was that only a little coloring of the reaction liquid was seen, but that the selectivity of the diethylene glycol monoacrylate and the selectivity of the diester were both low.

Example 9

The reaction was carried out in the same way as of Example 8 except that the whole acrylic acid was introduced into the first reactor without being divided.

After continuing to supply the ethylene oxide and the acrylic acid until the composition at the outlet of the second reactor became constant, the reaction product flowing out of the outlet of the second reactor was analyzed by gas chromatography. The results are as follows:

| | |
|---|---|
| Conversion of acrylic acid: | 74 mol % |
| Conversion of ethylene oxide: | 69 mol % |
| Molar ratio of ethylene oxide/acrylic acid: | 1.9 |
| Selectivity of diethylene glycol monoacrylate: | 3.0 mol % |
| Selectivity of diester: | 0.34 mol % |

The result was that only a little coloring of the reaction liquid was seen, but that the selectivity of the diethylene glycol monoacrylate and the selectivity of the diester were both low.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for a hydroxyalkyl ester, which comprises the step of carrying out a reaction between a carboxylic acid and an alkylene oxide in the presence of a catalyst, with the production process being characterized in that the reaction is carried out in a reaction liquid under conditions where a relationship a<b is kept throughout the reaction wherein "a" is a molar concentration (mol %) of the carboxylic acid in the reaction liquid and wherein "b" is a molar concentration (mol %) of the alkylene oxide in the, reaction liquid.

2. A production process according to claim 1, wherein the reaction is continuously carried out while a conversion of the alkylene oxide is kept in the range of 10~98 mol % and while a conversion of the carboxylic acid is kept in the range of 70~99 mol %.

3. A production process according to claim 2, which further comprises the steps of recovering an unreacted residue of the alkylene oxide and/or an unreacted residue of the carboxylic acid and then recycling said residue as raw reaction materials for the hydroxyalkyl ester.

4. A production process according to claim 1, wherein the catalyst is a basic resin.

5. A production process according to claim 4, wherein the basic resin has a heat-resistant temperature of not lower than 70° C.

6. A production process according to claim 4, wherein the basic resin is such that a water-humidified catalyst which is obtained by an immersion test of the basic resin cannot pass through a screen of 48 mesh in a ratio of not less than 80 vol % of what the water-humidified catalyst is before the test, wherein the screen of 48 mesh is designated by Tyler and includes a mesh opening size of 297 µm.

7. A production process according to claim 4, wherein the basic resin is such that a water-humidified catalyst which is obtained by an abrasion test of the basic resin cannot pass through a screen of 48 mesh in a ratio of not less than 80 vol % of what the water-humidified catalyst is before the test, wherein the screen of 48 mesh is designated by Tyler and includes a mesh opening size of 297 µm.

8. A production process according to claim 4, wherein the basic resin is such that a ratio of a cracked resin in a solvent-swollen catalyst which is obtained by a solvent displacement test of the basic resin is not more than 50%.

9. A production process according to claim 1, which further comprises the steps of dividing an amount of the carboxylic acid into at least two portions and then supplying said at least two portions to a reactor, with one portion of said at least two portions being supplied to the reactor at a first time and with another portion of said at least two portions being supplied to the reactor at a second time.

10. A production process according to claim 9, involving the use of one reactor to which the at least two portions of the carboxylic acid are supplied.

11. A production process according to claim 9, involving the use of at least two reactors to which respectively the at least two portions of the carboxylic acid are supplied.

12. A production process according to claim 1, wherein the carboxylic acid and the alkylene oxide which are starting materials are used in a ratio such that the alkylene oxide as charged is in a range of 1.0–5.0 mols per 1 mol of the carboxylic acid as charged.

13. A production process according to claim 1, wherein the carboxylic acid is (meth)acrylic acid.

14. A production process according to claim 3, wherein the catalyst is a basic resin.

15. A production process according to claim 14, which further comprises the steps of dividing the carboxylic acid into at least two portions and then supplying said portions to a reactor, with one said portion being supplied to the reactor at a first time and with said other portion being supplied to the reactor at a second time.

16. A production process according to claim 9, wherein the carboxylic acid and the alkylene oxide which are starting raw materials are used in a ratio such that the alkylene oxide as charged is in a range of 1.0–5.0 mols per 1 mol of carboxylic acid as charged.

17. A production process according to claim 15, wherein the carboxylic acid and the alkylene oxide which are starting raw materials are used in a ratio such that the alkylene oxide as charged is in a range of 1.0–5.0 mols per 1 mol of the carboxylic acid as charged.

18. A production process according to claim 9, wherein the carboxylic acid is (meth)acrylic acid.

19. A production process according to claim 15, wherein the carboxylic acid is (meth)acrylic acid.

20. A production process for a hydroxyalkyl ester comprising the steps of:
   a) carrying out a reaction in a reaction liquid between a carboxylic acid and an alkylene oxide in the presence of a catalyst;
   b) monitoring a molar concentration of carboxylic acid and a molar concentration of alkylene oxide during the reaction, wherein "a" is a molar concentration (mol %) of the carboxylic acid in the reaction liquid and wherein "b" is a molar concentration (mol %) of the alkylene oxide in the reaction liquid; and
   c) maintaining a relationship a<b throughout the reaction such that the molar concentration of alkylene oxide is in excess throughout the reaction.

* * * * *